United States Patent [19]

Carver et al.

[11] Patent Number: 5,007,741

[45] Date of Patent: Apr. 16, 1991

[54] METHODS AND APPARATUS FOR DETECTING IMPURITIES IN SEMICONDUCTORS

[75] Inventors: Gary E. Carver, Flemington, N.J.; Gregory L. Koos, Yardley; John D. Michalski, Furlong, both of Pa.

[73] Assignee: AT&T Bell Laboratories, Murray Hill, N.J.

[21] Appl. No.: 412,043

[22] Filed: Sep. 25, 1989

[51] Int. Cl.⁵ .............................................. G01N 21/55
[52] U.S. Cl. .................................. 356/448; 356/369; 356/346
[58] Field of Search ..................... 356/448, 445–447, 356/364, 369, 433, 346, 301

[56] References Cited

U.S. PATENT DOCUMENTS

| | | | |
|---|---|---|---|
| 3,600,099 | 8/1971 | Schoeffel | 356/448 |
| 3,623,818 | 11/1971 | Gardner | 356/448 |
| 4,444,499 | 4/1984 | Akiyama et al. | 356/448 |
| 4,590,574 | 5/1986 | Edmonds et al. | 356/346 |

OTHER PUBLICATIONS

"Analysis of Infrared Spectra for Oxygen Measurements in Silicon", by R. K. Graupner, Silicon Processing, ASTM STP 804, D. C. Gupta, Ed., *American Society for Testing and Materials*, 1983, pp. 459–468.

*Primary Examiner*—Richard A. Rosenberger
*Assistant Examiner*—Hoa Q. Pham
*Attorney, Agent, or Firm*—R. B. Anderson

[57] ABSTRACT

The purpose of the invention is to detect impurities in a semiconductor wafer (20). A laser (21) forms a light beam having a high proportion of its power at an optical frequency capable of being absorbed by the impurity to be measured. The beam is split into first (25) and second (26) light components, one of which is directed at the surface of the semiconductor wafer (20) to be tested and the other at a reference semiconductor wafer (27) containing a known quantity of the impurity to be measured. The light intensities reflected from the two wafers is detected by photodetectors (29, 30) and their difference is taken as a factor in measuring the impurity density in the wafer under test. A polarizer (33) polarizes the beam such as to maximize p-type component and minimize s-type components. Reflection from each of the two wafers (20, 27) is at the principal angle.

8 Claims, 3 Drawing Sheets

METHODS AND APPARATUS FOR DETECTING IMPURITIES IN SEMICONDUCTORS

TECHNICAL FIELD

This invention relates to methods and apparatus for detecting small amounts of materials in semiconductors, and, more particularly, to methods and apparatus for detecting and measuring trace interstitial impurities in crystalline semiconductor wafers.

BACKGROUND OF THE INVENTION

As the complexity of semiconductor integrated circuits grows and as the circuit densities defined on semiconductor integrated circuits increase, it becomes increasingly important to characterize accurately the precise nature of the semiconductor wafer from which integrated circuit chips are made. For example, silicon wafers made by the liquid encapsulated Czochralski process typically contain trace interstitial oxygen of a concentration of typically $1 \times 10^{18}$ atoms per cubic centimeter. These trace impurities are not necessarily harmful and, in fact, are sometimes used by process engineers as "gettering" sites, that is, sites for neutralizing other unwanted impurities. However, since too great a concentration of interstitial oxygen would harm device performance, it is common to specify the range of concentration or density of interstitial oxygen required in the wafers to be used.

One way of measuring interstitial oxygen in a silicon wafer is to direct light of an appropriate wavelength through the wafer. Since interstitial oxygen absorbs light of a characteristic wavelength, its concentration can be measured by measuring the proportion of light at that characteristic wavelength transmitted through the wafer. A drawback of this method is that it cannot be used for measuring interstitial oxygen in highly doped silicon wafer because such doping tends to make the wafer opaque. "Doping" refers to the impregnation of the silicon crystal with impurities such as phosphorous or boron which determine its current-carrying capabilities. Vendors of silicon wafers often measure the interstitial oxygen in an undoped wafer and then assume that the interstitial oxygen concentration in a highly doped wafer made by the same crystal growth process will be the same. Unfortunately, this assumption is often not correct. In fact, papers in the literature indicate that interstitial oxygen concentration is often changed by the type and concentration of conductivity-determining impurities used in doping the wafer.

Highly doped silicon wafers can be tested for interstitial oxygen by various destructive techniques known in the art, such as secondary ion mass spectroscopy (SIMS), charged particle activation analysis (CPAA), or gamma ray activation analysis. For the sake of brevity, these techniques will not be reviewed, but they are all generally unsatisfactory in that they require destruction or some sort of structural damage to at least part of the wafer in order to determine interstitial oxygen concentration. There has, therefore, been a recognized need in the art for a method to detect, conveniently, accurately and non-destructively, trace interstitial oxygen in silicon wafers, especially highly doped silicon wafers, i.e., wafers having a doping concentration in excess of about $1.0 \times 10^{18}$ conductivity-determining atoms per cubic centimeter.

SUMMARY OF THE INVENTION

Our invention is a consequence of several important insights and findings: first, the absorption of certain optical frequencies by interstitial impurities will also affect the reflectivity of light from the surface of the semiconductor wafer at such frequencies; secondly, small changes of reflectivity due to the presence of an interstitial impurity can be detected by comparing the light reflected from such a surface with light reflected from a semiconductor wafer having a known quantity of such impurity; third, these effects can be made more pronounced by using polarized light and by reflecting the light from the surfaces at the principal angle of reflection.

In one illustrative embodiment, a laser forms a light beam having a high proportion of its power at an optical frequency capable of being absorbed by the impurity to be measured. The beam is split into first and second light components, one of which is directed at the surface of the semiconductor wafer to be tested, and the other at a reference semiconductor wafer containing a known quantity of the impurity to be measured. The light reflected from the two wafers is detected by photodetectors, and the difference of energy detected from the two beam components is taken as a measurement of impurity density in the wafer under test. Specifically, the difference in detected energy is a consequence of a difference of reflectivity of the two wafers, which is an indicator of impurity density.

Several techniques are preferably used to enhance detection of the small difference in reflectivity caused by the impurity to be measured. The light is preferably light which has been polarized to contain predominantly the "p-type" polarization and the angle at which it is reflected, from both the wafer under test and the reference wafer, is equal to the principal angle of reflection. As is known, at this angle, p-type light is reflected with exceedingly low efficiency, but nevertheless, such reflection is preferred for indicating the density of the impurity, as will be explained later. Detection of small optical energy differences is enhanced by chopping the laser beams prior to reflection from the wafer surfaces. In one embodiment, the reflected light components are combined in a beam splitter and are detected by a single photodetector. Light reflected from the two surfaces is distinguished by alternately chopping the two light components and using a computer to determine from which of the two surfaces each reflected light pulse originated.

In the preferred embodiment, the semiconductor is crystalline silicon and the impurity to be detected is interstitial oxygen. Either a carbon dioxide laser or a lead-salt diode laser will produce light within the characteristic oxygen absorption band 8.9–9.15 microns. The detection of the interstitial oxygen is nondestructive of the wafer and produces accurate results even if the silicon wafer is highly doped and even if the wafer is completely opaque at the absorption band.

These and other objects, features, and advantages of the invention will be better understood from a consideration of the following detailed description taken in conjunction with the accompanying drawings.

DETAILED DESCRIPTION

Figure 1:
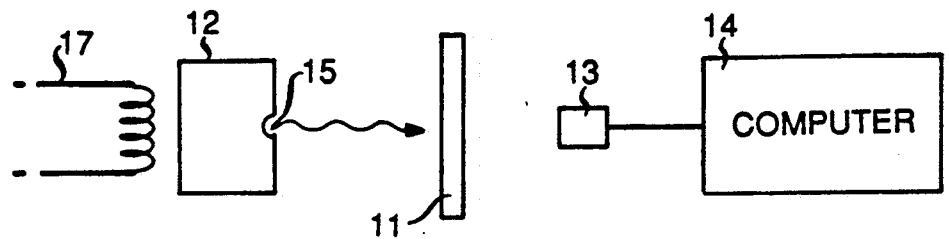
FIG. 1 is a schematic view of apparatus for determining interstitial oxygen in silicon wafers having a low doping level, in accordance with the prior art.
Figure 2:
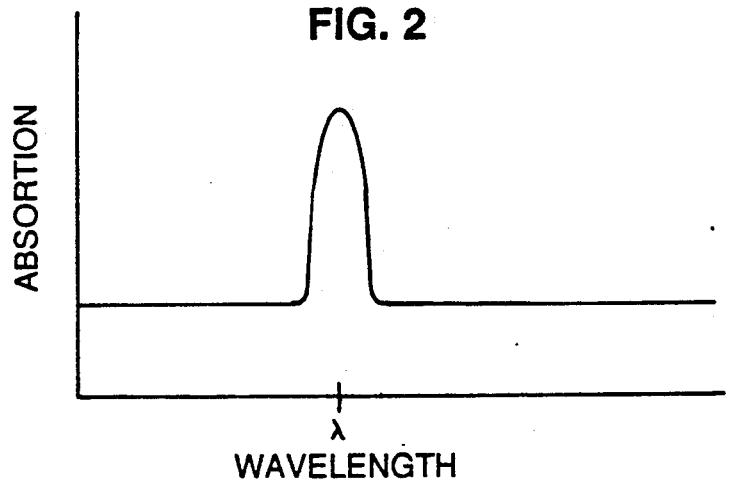
FIG. 2 is a graph of optical absorption in the silicon wafer of FIG. 1 versus optical wavelength for a given amount of interstitial oxygen.

Referring now to FIG. 1, there is shown apparatus in accordance with the prior art for detecting interstitial oxygen in a silicon wafer 11 which comprises a light source 12, a photodetector 13 and a computer 14. As shown in FIG. 2, it is known that interstitial oxygen absorbs light within a narrow band containing a maximum absorption wavelength $\lambda$ of 9.04 microns. Any of a number of light sources can be used for emitting light of this wavelength, but the source 12 illustratively shown in FIG. 1 comprises a "black body" source which may be a carbon block or "glowbar" having a 0.25 inch hole 15 and heated to a temperature of 900° C. by a heater schematically shown as heater 17. This may produce one milliwatt of power in the oxygen absorption band (8.9–9.15 microns). The computer 14 is programmed to give an indication of interstitial oxygen in accordance with the light intensity transmitted through the wafer 11 at the absorption band of interstitial oxygen. As mentioned previously, this prior art method will not work with wafers that are highly doped, because such wafers become opaque at frequencies centered about the wavelength $\lambda$ at doping levels in excess of about $1.0 \times 10^{18}$ atoms per cubic centimeter.

Figure 3:
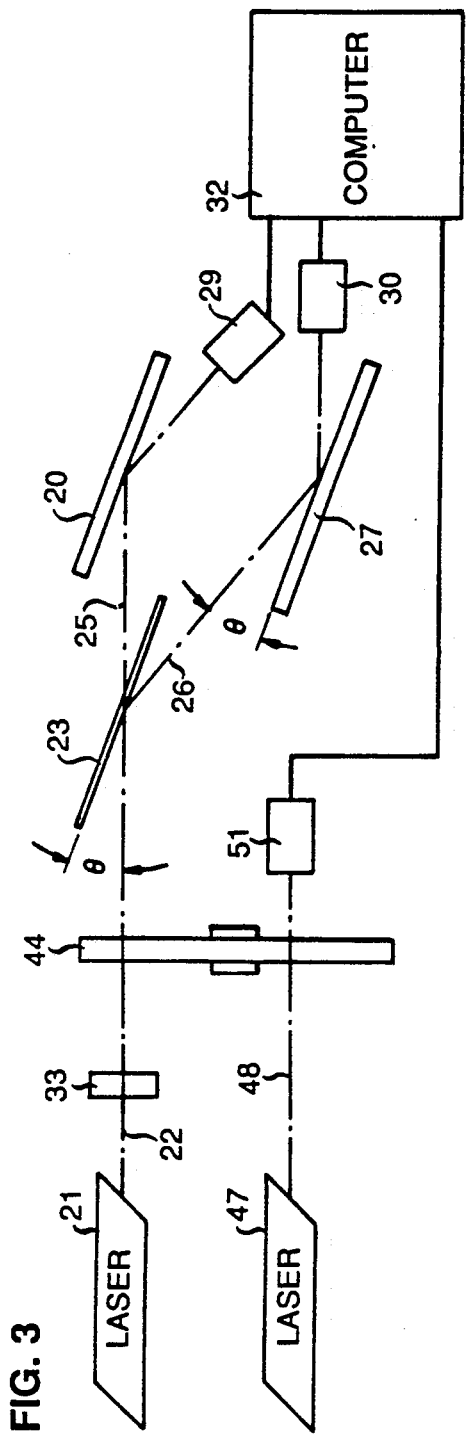
FIG. 3 is a schematic view of apparatus for measuring impurities in a semiconductor wafer in accordance with one embodiment of the invention.

Referring to FIG. 3, the invention makes use of an arrangement, similar to known Mach-Zehnder interferometer arrangement, for measuring interstitial oxygen in a highly doped silicon wafer 20. A laser 21 generates a light beam 22 which contains optical power in the oxygen absorption band of 8.9–9.15 microns. Such a laser may, for example, be a carbon dioxide laser or a lead-salt diode laser or laser array. As is known, the carbon dioxide laser frequency can be tuned and the lead-salt diode can be tuned somewhat by temperature variation, and such tuning should be used to maximize laser power in the oxygen absorption band. The beam 22 is divided by a beam splitter 23 into a first component 25 that is reflected from the surface of wafer 20 to be tested and a second component 26 that is reflected from a reference silicon wafer 27, having in it a known density of interstitial oxygen atoms. The first light beam component reflected from wafer 20 is detected by photodetector 29 and the second light component reflected from reference wafer 27 is detected by photodetector 30. The output of photodetector 29 is compared with that of photodetector 30 in a computer 32 to give an indication of interstitial oxygen in wafer 20.

It should be noted that the beam path 22 makes an angle $\theta$ with beam splitter 23, and the first and second light components likewise have paths that make an angle $\theta$ with wafers 20 and 27. The purpose of these angles is to cause the light beam components 25 and 26 to be reflected at the principal angle of reflection from the wafer surfaces. The light produced by laser 21 is polarized and filtered by a polarizer 33 such that it contains only the p-type component. As is known in the art, p-type refers to light that is polarized within the plane of incidence, while light polarized perpendicular to the plane of incidence is known as s-type. By definition, the principal angle is that at which light of p-type polarization is minimally reflected. It is also sometimes referred to as the Brewster angle.

Figure 5:
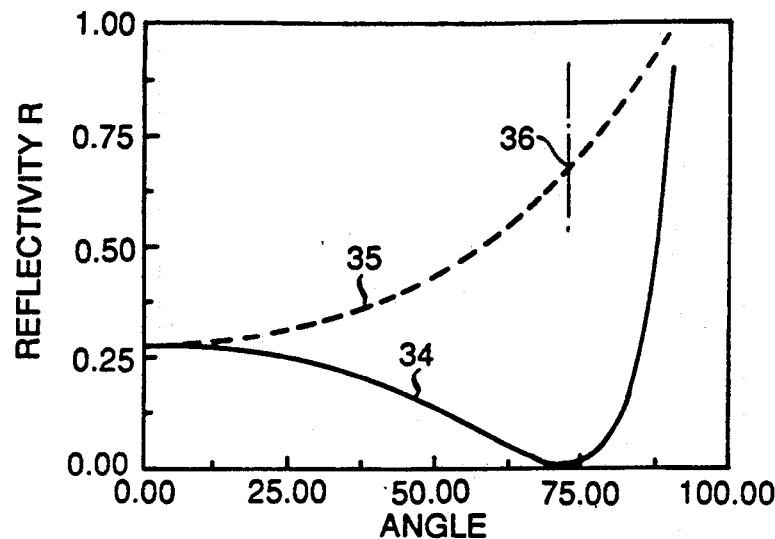
FIG. 5 is a graph of optical reflectivity versus angle of reflection from the semiconductor wafer under test of the apparatus of FIG. 3.

Referring to FIG. 5, the solid curve 34 shows the reflectivity R of p-type light with respect to the angle of incidence, while curve 35 illustrates the reflectivity of s-type polarized light. Reflectivity R is the ratio of intensities of reflected light to incident light. Note that at the principal angle, which in this case is an angle of incidence of approximately 73°, any s-type polarized light has a reflectivity shown by point 36 while the p-type light has a reflectivity that is exceedingly low, typically 0.001. This illustrates the known fact that at the principal angle, light of p-type polarization is minimally reflected from the surface.

Figure 6:
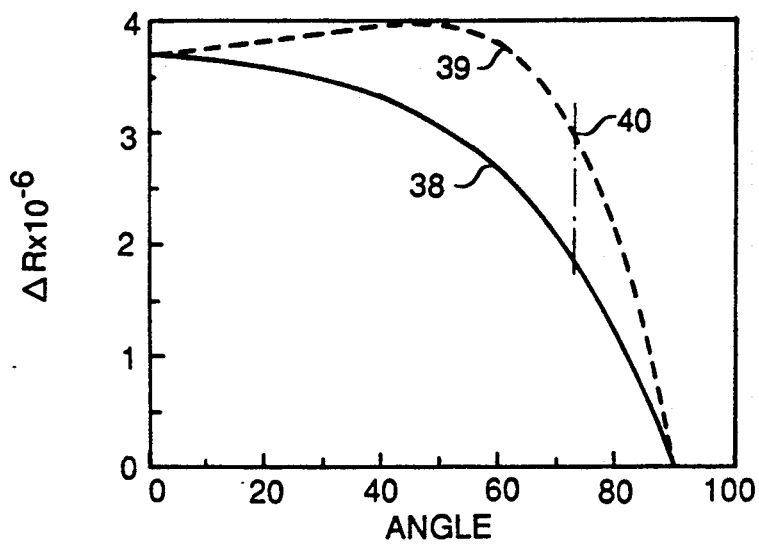
FIG. 6 is a graph of the change of reflectivity due to impurities versus angle of reflection from the semiconductor wafer under test of the apparatus of FIG. 3.

The graph of FIG. 6 shows the differential reflectivity $\Delta R$ due to twenty parts per million of interstitial oxygen in silicon for the p-type polarization of curve 38 and s-type polarization of curve 39. That is, the ordinate shows the difference ($\Delta R = R_1 - R_2$) of the reflectivity $R_1$ of the reference wafer and the reflectivity $R_2$ of the wafer under test, in terms multiplied by $10^{-6}$. Note that at the principal of angle shown by location 40, the differential reflectivity of the s-type polarization is significantly higher than that of the p-type.

Figure 7:
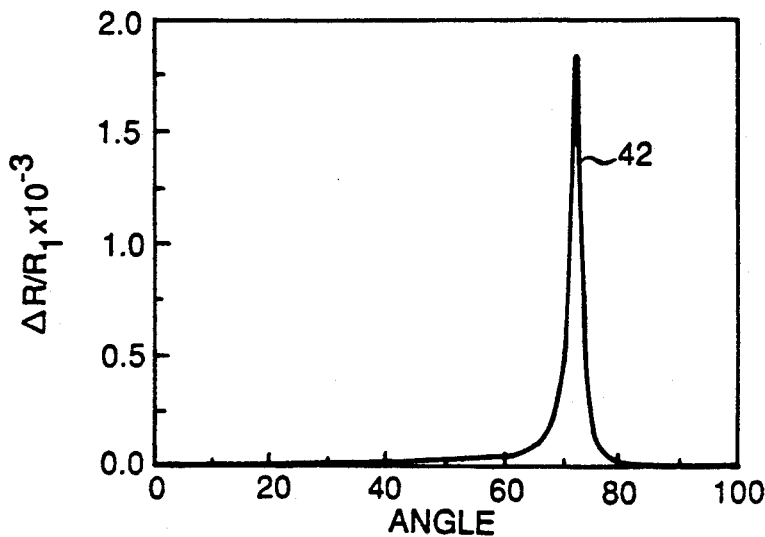
FIG. 7 is a graph of the change of reflection due to impurities divided by total reflection versus angle of reflection from the semiconductor wafer under test of the apparatus of FIG. 3.

FIG. 7 shows a graph 42 of the normalized differential p-type reflectivity $\Delta R/R_1$ due to twenty parts per million of oxygen in silicon. Curve 42 shows a sharp peak at the principal angle (in this case, 73°) and it also shows that a value of $\Delta R/R_1$ of nearly $2 \times 10^{-3}$ is detected with an interstitial oxygen density of only twenty parts per million. The graph of FIG. 7 shows that the reflected light should be measured at the principal angle of reflection and that significant variations of $\Delta R/R_1$ can be observed as a function of small amounts of interstitial oxygen. Further it can be shown that $\Delta R/R_1$, varies in direct proportion to interstitial oxygen density. Thus, with twenty parts per million producing $\Delta R/R_1$, of about $1.8 \times 10^{-3}$, ten part per million would produce a value of about $0.9 \times 10^{-3}$.

Note that in FIG. 3, the angle $\theta$ is the complement of the principal angle, viz., 17°. The graphs of FIG. 5 and 6 also indicate that since s-type polarized light is reflected with much more efficiency than p-type, the s-type light should be minimized. Polarizer 33 is made in a known manner so as to filter or minimize the s-type component.

Figure 4:
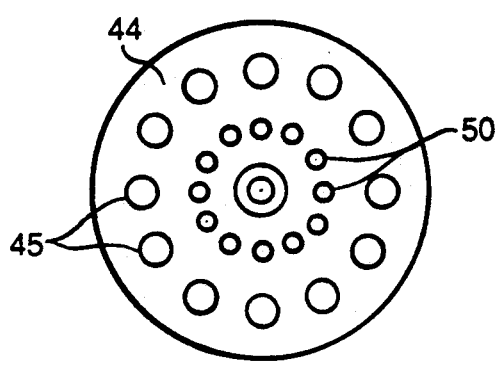
FIG. 4 is a front view of the chopper wheel of FIG. 3.

As is known, the light intensities detected by photodetectors 29 and 30 are directly proportional to $R_1$ and $R_2$ and can therefore be used, with the computer, to give an indication of $\Delta R/R_1$. To reduce the effects of fluctuations in laser power or detector sensitivity, the light beam 22 should be chopped so as to generate alternating currents that can be processed by amplifiers in computer 32. For this purpose, a rotating chopper wheel 44 is included in the apparatus of FIG. 3 to block periodically laser beam 22 so as to give it a predictable alternating frequency. Referring to FIG. 4, the wheel 44 may have a plurality of openings 45 that successively permit transmission of the beam as the wheel rotates, with the beam being blocked between such transmissions. The computer 32 can be synchronized with the light beam pulses through the use of a laser 47 shown in FIG. 3 that directs a light beam through apertures 50 in the chopper wheel 44 which are detected by photodetector 51. The pulses detected by 51 then synchronize the computer with the pulses delivered by photodetectors 29 and 30.

The computer 32 can be programmed to give direct readings of interstitial oxygen either empirically, that is, by using readings from numerous wafers having known quantities of interstitial oxygen, or theoretically, by mathematically determining the changes in reflectivity due to interstitial oxygen. In making theoretical determinations, it is known that absorption $\alpha$ is related to interstitial oxygen density $[O_i]$ by the relation, $$\alpha = [O_i]/\gamma \quad (1)$$

where $\gamma$ equals $3.44 \times 10^{17}$ cm$^{-2}$. Values for $\Delta k$, the differential complex component of the index of refraction of silicon, is related to differential absorption by, $$\Delta \alpha = 4\pi \Delta k / \lambda \quad (2)$$

Using Fresnel's equations as a function of angle, one can then obtain reflectivity $R_1$, change of reflectivity $\Delta R$ and $\Delta R/R_1$ for various values of interstitial oxygen density. Thus, the interstitial oxygen density is determined directly by dividing the difference of light intensities detected by photodetectors 29 and 30 by the intensity detected by detector 30.

Typical values of $\Delta R$ are in the $10^{-6}$ range. Assuming an angle of incidence of 73°, a 9.04 micron light source of five milliwatts, a detector responsivity of 1,000 volts per watt, and a preamplifier gain of 100, one can predict a signal ($\Delta R$) of about one millivolt. This voltage is in mid-range for commercially available "lockin" amplifiers and is about 100 times the minimum signal for known HgCdTe (mercury cadmium telluride) photodetectors.

Figure 8:
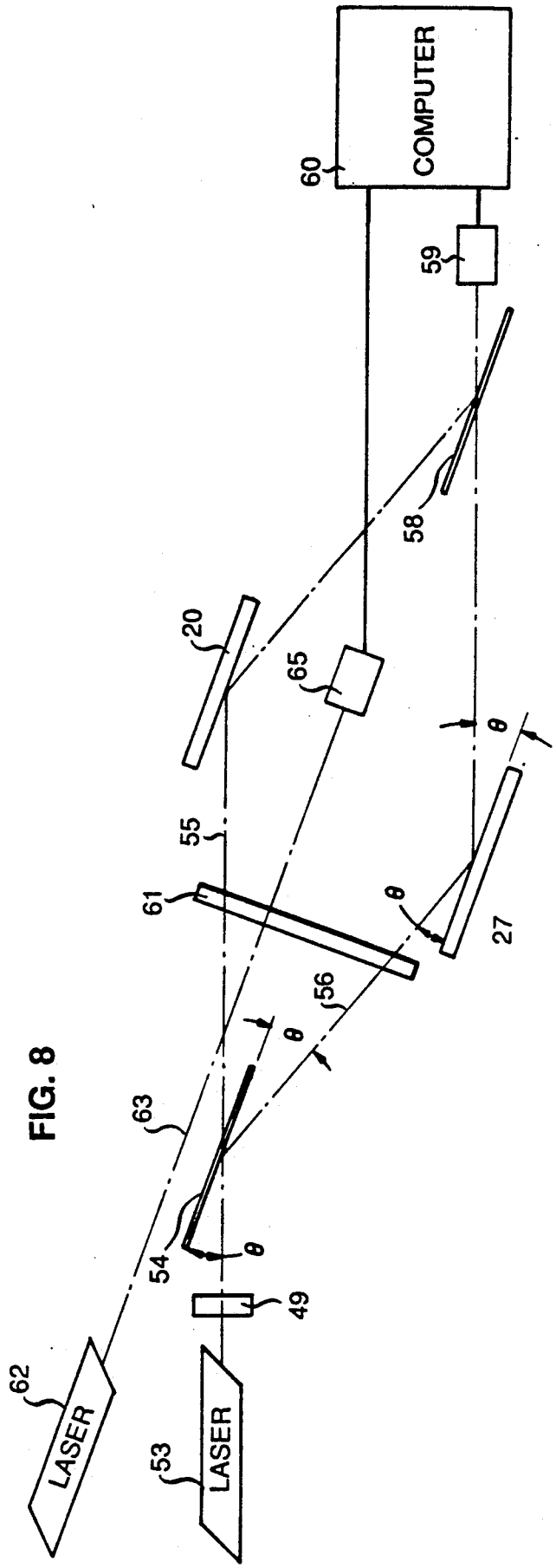
FIG. 8 is a schematic view of apparatus for detecting impurities in a semiconductor wafer in accordance with another embodiment of the invention.

Referring to FIG. 8, there is shown another embodiment of the invention that works on the same principle, but only requires a single photodetector for collecting light from both light components. Light formed by a laser 53 and polarized as before by a polarizer 49 is divided by a beam splitter 54 into components 55 and 56. As before, wafer 20 is a wafer under test and wafer 27 is the reference wafer. After reflection, both components 55 and 56 are combined in a beam splitter 58 with the combined beam being detected by a single detector 59. In order to permit the computer 60 to distinguish between light reflected from wafer 20 and that reflected from wafer 27, the chopper wheel 61 is located so as to alternately chop the two light components 55 and 56; that is, the light of the first component 55 is blocked as that of the second component 56 is being transmitted, and vice versa. A laser 62 directs a beam 63 through synchronizing apertures on the chopper wheel 61 that are detected by photodetector 65. The signal generated by photodetector 65 is used by computer 60 for synchronization and to distinguish between light of the first component 55 reflected from wafer 20 and light from the second component 56 reflected from wafer 27. Our calculations show that for this embodiment, the timing of the pulses is of crucial importance in that measurements cannot be made during the transition period when either light components 55 or 56 are partially blocked.

It should be noted that since light is not transmitted through wafer 20 under test, our invention does not give an indication of interstitial oxygen in the bulk of the wafer. Instead, our calculations show that it is affected by oxygen concentration to a depth of about four microns from the surface of the wafer. Before thermal treatments, this surface value will be dependably representative of oxygen density in the bulk.

We have shown how comparative reflectivity measurements can be used in a practical manner to give an accurate measurement of interstitial oxygen ($[O_i]$) in crystalline silicon. By using polarized light reflected at the principal angle, we are able to emphasize small differential reflectances so they can be measured. Various lasers are the most practical sources of light within a narrow band of frequencies, but in principle other light sources such as "glowbars" could be used. Filtering the s-type polarized light is strongly preferred, but in principle is not essential. Chopping the laser light is not required in principle, but it greatly simplifies the electronics needed for detection. Likewise, the separate generation of timing pulses simplifies the electronics.

We have concentrated on the detection of interstitial oxygen in silicon, but it is likely that the invention could be used for detecting other impurities in other semiconductors. One would, of course, need to match the optical frequency generated by the laser to the absorption band of the impurity to be detected. Various other embodiments and modifications may be made by those skilled in the art without departing from the spirit and scope of the invention.

What is claimed is:

1. A method for detecting and measuring a specific impurity which is not a conductivity-determining impurity in a crystalline semiconductor wafer comprising the steps of:

forming a light beam containing an optical frequency capable of being absorbed by the specific impurity;

polarizing the beam such that it contains light predominantly of a p-type polarization;

splitting the beam into first and second light components;

directing the first light component at a first semiconductor wafer containing an unknown density of the specific impurity;

directing the second light component at a second semiconductor wafer containing a known density of the specific impurity;

the first and second light components being respectively directed at the first and second wafers at an angle of incidence substantially equal to the principal angle of incidence;

detecting p-type polarized light of the first light component reflected from the first water;

detecting p-type polarized light of the second light component reflected from the second wafer;

measuring the difference of intensity of the detected first and second p-type polarized light components;

and using the measured intensity difference to determine the density of the specific impurity contained in the first wafer.

2. The method of claim 1 further characterized in that:
   reflected light from the first and second wafers is combined in a beam splitter prior to detection.

3. The method of claim 7 further characterized in that:
   separate photodetectors are used to detect the reflected first and second light components;
   and the chopping step comprises the step of chopping the light beam before it is split into components.

4. The method of claim 1 wherein:
   the step of determining the density of the specific impurity includes the step of using a computer to divide the difference of intensity of the detected first and second light components by the intensity of the detected second light component.

5. The method of claim 4 wherein:
   the light beam is taken from a laser; and before the detecting step, the first and second light components are chopped.

6. The method of claim 5 wherein:
   the first and second semiconductor wafers are both of silicon;
   the impurity to be detected is interstitial oxygen;
   and the light beam contains light having a wavelength in the range of 8.8–9.2 microns.

7. The method of claim 6 wherein:
   the first and second semiconductor wafers are both doped with conductivity-determining impurity to a concentration in excess of about $10^{18}$ atoms per cubic centimeter.

8. The method of claim 7 wherein:
   the first and second light components are respectively directed at the first and second wafers at an angle of incidence equal approximately to the principal angle.

* * * * *